(12) United States Patent
Gerard et al.

(10) Patent No.: US 9,237,929 B2
(45) Date of Patent: Jan. 19, 2016

(54) SYSTEM FOR GUIDING A MEDICAL INSTRUMENT IN A PATIENT BODY

(75) Inventors: Olivier Gerard, Viroflay (FR); Raoul Florent, Ville D'Avray (FR); Geert Gijsbers, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 3066 days.

(21) Appl. No.: 10/596,434

(22) PCT Filed: Dec. 17, 2004

(86) PCT No.: PCT/IB2004/004225
§ 371 (c)(1),
(2), (4) Date: Jun. 13, 2006

(87) PCT Pub. No.: WO2005/063125
PCT Pub. Date: Jul. 14, 2005

(65) Prior Publication Data
US 2007/0276243 A1    Nov. 29, 2007

(30) Foreign Application Priority Data

Dec. 22, 2003 (EP) .................................... 03300279
Mar. 22, 2004 (EP) .................................... 04300157

(51) Int. Cl.
*A61B 19/00* (2006.01)
*A61B 6/12* (2006.01)
*A61B 8/12* (2006.01)
*A61B 8/08* (2006.01)
*A61B 6/00* (2006.01)
*A61B 8/00* (2006.01)

(52) U.S. Cl.
CPC . *A61B 19/20* (2013.01); *A61B 6/12* (2013.01); *A61B 6/469* (2013.01); *A61B 6/5247* (2013.01); *A61B 8/0833* (2013.01); *A61B 8/4245* (2013.01); *A61B 8/483* (2013.01); *A61B 8/5238* (2013.01); *A61B 8/5276* (2013.01); *A61B 19/52* (2013.01); *A61B 19/5244* (2013.01); *A61B 6/463* (2013.01); *A61B 8/0841* (2013.01); *A61B 8/12* (2013.01); *A61B 8/42* (2013.01); *A61B 8/4227* (2013.01); *A61B 8/44* (2013.01); *A61B 19/54* (2013.01); *A61B 2019/5238* (2013.01);
(Continued)

(58) Field of Classification Search
CPC ........ A61B 8/12; A61B 8/0841; A61B 8/466; A61B 8/5238; A61B 6/463; A61B 8/42; A61B 8/44
USPC ........................................................ 600/407
See application file for complete search history.

(56) References Cited

U.S. PATENT DOCUMENTS

5,357,550 A * 10/1994 Asahina et al. .............. 378/98.5
5,368,032 A * 11/1994 Cline et al. ................... 600/411
(Continued)

Primary Examiner — Tse Chen
Assistant Examiner — Vani Gupta (57) ABSTRACT

The present invention relates to a system for guiding a medical instrument in a patient body. Such a system comprises means for acquiring a 2D X-ray image of said medical instrument, means for acquiring a 3D ultrasound data set of said medical instrument using an ultrasound probe, means for localizing said ultrasound probe in a referential of said X-ray acquisition means, means for selecting a region of interest around said medical instrument within the 3D ultrasound data set and means for generating a bimodal representation of said medical instrument detection by combining said 2D X-ray image and said 3D ultrasound data set. A bimodal representation is generated on the basis of the 2D X-ray image by replacing the X-ray intensity value of points belonging to said region of interest by the ultrasound intensity value of the corresponding point in the 3D ultrasound data set.

14 Claims, 11 Drawing Sheets

(52) U.S. Cl.
CPC . *A61B2019/5251* (2013.01); *A61B 2019/5276* (2013.01); *A61B 2019/5291* (2013.01)

(56) References Cited

U.S. PATENT DOCUMENTS

| | | | |
|---|---|---|---|
| 5,810,007 A | 9/1998 | Holupka et al. | |
| 6,233,477 B1 * | 5/2001 | Chia et al. | 600/424 |
| 6,351,513 B1 | 2/2002 | Bani-Hashemi et al. | |
| 6,546,279 B1 | 4/2003 | Bova et al. | |
| 6,558,333 B2 * | 5/2003 | Gilboa et al. | 600/466 |
| 6,574,492 B1 * | 6/2003 | Ben-Haim et al. | 600/374 |
| 7,505,809 B2 * | 3/2009 | Strommer et al. | 600/424 |
| 2001/0029334 A1 | 10/2001 | Graumann et al. | |
| 2004/0254454 A1 * | 12/2004 | Kockro | 600/424 |

* cited by examiner

SYSTEM FOR GUIDING A MEDICAL INSTRUMENT IN A PATIENT BODY

FIELD OF THE INVENTION

The present invention relates to a medical system comprising a medical instrument to be guided in a patient body and means for visualizing said medical instrument. The invention also relates to a method to be used in said system. The invention finds for example its application for guiding a catheter inside the heart of a patient during an electrophysiology interventional procedure.

BACKGROUND OF THE INVENTION

Clinical applications in which a medical instrument has to be guided into the body of a patient are becoming widespread. Notably the growing interest in minimal-invasive methods for the treatment of cardiac diseases necessitates the development of methods and devices allowing the physician to guide a medical instrument to predetermined positions inside or outside the heart. In electrophysiology for example, it is necessary to guide a catheter to a plurality of predetermined positions on the ventricular or atrial walls in order to measure an electrical pulse or to burn wall tissues.

U.S. Pat. No. 6,587,709 discloses a system for guiding a medical instrument in the body of a patient. Such a system acquires a live 3D ultrasound image data set using an ultrasound probe. An advantage of acquiring a 3D image data set is to get depth information. An advantage of using a live 3D ultrasound image modality is that the surrounding anatomy is visible, which facilitates the guidance of the medical instrument by the physician. The system further comprises localization means for localizing the medical instrument within the 3D ultrasound data set, which locates three ultrasound receivers mounted on the medical instrument relatively to said ultrasound probe. Such a localization allows an automatic selection of a plane to be imaged, which comprises at least a section of the medical instrument. Therefore no readjustment of the ultrasound probe position by hand is necessary.

A first drawback of such a 3D ultrasound data set is that it has a narrow viewing field, which does not cover the whole part of the patient body concerned by a catheter introduction and placement. Therefore, for guiding the catheter during the whole procedure, the ultrasound probe has to be moved several times. At each displacement, a pre-operative step of locating the ultrasound probe in a referential of the interventional room is needed, because the location of the catheter is measured relatively to the ultrasound probe location. Such a pre-operative step may delay and complicate the interventional procedure.

A second drawback of the ultrasound imaging modality is that it has a low resolution Therefore, the acquired 3D ultrasound data set does not give an image of the catheter and its surrounding of acceptable quality.

A third drawback of the ultrasound imaging modality is that there are some zones of the patient body where the thoracic cage blocks the ultrasound scan and no exploitable image can be output.

SUMMARY OF THE INVENTION

The object of the invention is therefore to provide a medical system for guiding a medical instrument in a patient body, which gives an improved visibility of the medical instrument and its surrounding anatomy during the whole procedure.

This is achieved by a medical system comprising:
a medical instrument to be guided in a patient body,
X-Ray acquisition means for acquiring a two-dimensional X-ray image of said medical instrument,
ultrasound acquisition means for acquiring a three-dimensional ultrasound data set of said medical instrument using an ultrasound probe,
means for providing a localization of said ultrasound probe within a referential of said X-ray acquisition means,
means for selecting a region of interest around said medical instrument in the 3D ultrasound data set, that define a first localization of said region of interest within a referential of said ultrasound acquisition means,
means for converting said first localization of said region of interest within said referential of the ultrasound acquisition means into a second localization of said region of interest within said referential of the X-ray acquisition means, using said localization of the ultrasound probe,
means for generating and displaying a bi-modal representation of said medical instrument in which said two-dimensional X-ray image and the three-dimensional ultrasound data included in said region of interest are combined using said second localization.

With the invention, a bimodal representation is provided, in which two-dimensional (2D) X-Ray data and three-dimensional (3D) ultrasound data are combined. 2D X-ray data provide a good visibility and a high resolution of the medical instrument and of bone structures. 2D X-Ray data also benefit from a large viewing field, which allows a visualization of the whole area of the patient body concerned by the electrophysiology procedure.

3D ultrasound data provide a good visibility of soft tissues and sometimes vascularities in a surrounding of the medical instrument. In addition, 3D ultrasound data give an indication of depth, which is not provided by the 2D X-Ray image, because said X-Ray image only provides a projection of said medical instrument in accordance with a geometry of the X-Ray acquisition means. Such a geometry defines lines of projection, along which absorptions of X-rays by the exposed tissues of the patient are accumulated. Therefore, the visibility of the surrounding of the medical instrument is improved by the combination of the 2D X-Ray and the 3D ultrasound data.

In order to provide such a combination, the system firstly localizes the ultrasound probe and the 3D ultrasound data set in a referential of the X-Ray acquisition means. Such a referential of the X-ray acquisition means is supposed to be fixed. Therefore, assuming that the ultrasound probe does not move, a position of any point of the 3D ultrasound data set in said referential the X-ray acquisition means can be deduced. As the position of the 2D X-Ray image on the X-Ray detector within the referential of the X-Ray acquisition means is given by the geometry of the X-Ray acquisition means, the localization of the 3D ultrasound data set within the referential of the X-Ray acquisition means allows a mapping of the 3D ultrasound data set with the 2D X-Ray image, i.e. a mapping of a projection of any point of the 3D ultrasound data set in accordance with the geometry of the X-Ray acquisition means with a point of the 2D X-Ray image.

The system in accordance with the invention further selects a region of interest surrounding the medical instrument in the 3D ultrasound data set and provides a first localization of said region of interest within a referential of the ultrasound acquisition means. Such a selection, which is made either manually or automatically, aims at suppressing any ultrasound data which could occlude the visualization of the medical instrument.

The first localization, which is expressed with coordinates of a referential of the 3D ultrasound acquisition means, is then converted into a second localization of the medical instrument within the referential of the X-Ray acquisition means, using the localization of the ultrasound probe.

The system in accordance with the invention finally generates a bimodal representation, in which the 3D ultrasound data included in said region of interest are combined to the 2D X-Ray data using said second localization of the region of interest within the referential of the X-Ray acquisition means.

Preferably, the bimodal representation is generated on the basis of the 2D-X-ray image. In this 2D X-ray image all the X-ray intensity values of points having corresponding points in the selected region of interest of the 3D ultrasound data set are combined by the ultrasound intensity values.

Said means for selecting a region of interest are intended to define a reference plane in which a part of said medical instrument is included. In a first embodiment of the invention the region of interest is included into said reference plane which, for instance, comprises the extremity of the medical instrument which is in contact with the wall tissue and is perpendicular to the orientation of the X-Ray acquisition means. Therefore, the means for generating a bimodal representation are intended to combine the 2D X-Ray image with the 2D ultrasound image which is obtained by sampling the 3D ultrasound data set over the reference plane coordinates in the referential of the X-Ray acquisition means. A first advantage of the first embodiment of the invention is that it is very simple. A second advantage is that any ultrasound data which could occlude the medical instrument and its surrounding have been removed.

In an alternative, the selection means comprises detection means for detecting the medical instrument in the region of interest of the 3D ultrasound data set. Such a detection is for instance achieved automatically by using image processing techniques, for instance a filter for enhancing and thresholding elongated shapes. In the bimodal representation the X-ray intensity values of the points of the 2D X-ray image belonging to the detected medical instrument are advantageously kept unchanged. A first advantage is that the bimodal representation benefits from the high resolution of the medical instrument provided by the X-ray acquisition means.

A second advantage of this detection is that it is based on image processing techniques and does not require any specific medical instrument, like a medical instrument equipped with active localizers. Considering that the medical instrument has to be changed for each new patient, another advantage of the system in accordance with the invention is to allow a non negligible cost savings.

A third advantage of this detection is that it gives a localization of the extremity of the medical instrument. This localization, combined with the bimodal representation, may help generating of an electrical activation map of the heart cavity wall. As a matter of fact, in such a procedure, the medical instrument is a catheter equipped at its extremity with a sensor for measuring electrical pulses on a heart cavity wall. The user activates the sensor when the catheter is in contact with the heart cavity wall. A measurement of the electrical pulse at the current position of the catheter is made. The localization of the catheter provided by the system in accordance with the invention provides a location of the point corresponding to said current position and said electrical measurement in the electrical activation map. By visualizing the bimodal representation the user has the possibility to evaluate a distance between the current measurement point and previous measurement points. Therefore, the system in accordance with the invention facilitates a quick, uniform and complete mapping of the cavity wall.

In a second embodiment of the invention, the system in accordance with the invention further comprises means for segmenting a wall tissue region in the 3D ultrasound data set. Therefore, in the 2D X-ray image, only the X-ray intensity values of the points belonging to said wall tissue region are combined with the corresponding ultrasound intensity values. Therefore, the bimodal representation overweights X-Ray intensity values inside the cavity wall and ultrasound intensity values in and outside the cavity wall. An advantage is that the bimodal representation locally benefits from the best information available.

In a third embodiment of the invention, the region of interest is a 3D subset of the 3D ultrasound data set, which either lies behind the reference plane along the X-Ray direction or forms a slab around the reference plane. A volume rendered view of the 3D ultrasound data included in said selected region of interest is provided. The bimodal representation is built up by combining the intensity values of points of the 2D X-ray projection with the intensity values of the corresponding points in the volume rendered view. An advantage is to provide a perspective view of the surrounding tissues.

The system in accordance with the invention is capable of acquiring the 2D X-Ray image and the 3D ultrasound data set in real-time. Therefore, the medical instrument can be tracked in each new 2D X-Ray image and 3D ultrasound data set.

In a fourth embodiment of the invention, the system comprises controlling means for periodically triggering the probe localization means. As a matter of fact, the position of the ultrasound probe within the referential of the X-Ray acquisition means may be changed by external movements of the patient like respiratory movements during the clinical procedure. Therefore, the localization of the ultrasound probe has to be updated regularly.

In a fifth embodiment of the invention, the system comprises means for estimating and compensating a motion of a current 3D ultrasound data set acquired at a time t with respect to a previous 3D ultrasound data set acquired at a time t−1. An advantage is that small displacements of the ultrasound probe can be corrected without triggering the probe localization means and therefore without interrupting the live visualisation of the medical instrument.

These and other aspects of the invention will be apparent from and will be elucidated with reference to the embodiments described hereinafter.

BRIEF DESCRIPTION OF THE DRAWINGS

The present invention will now be described in more detail, by way of example, with reference to the accompanying drawings, wherein.

DETAILED DESCRIPTION OF THE INVENTION

The present invention relates to a system for guiding a medical instrument in a patient body. Such a system is particularly adapted for guiding a catheter within the heart cavities in order to diagnose and cure heart diseases, but it can more generally be used for guiding any other medical instrument in the patient body, like for instance a needle.

Figure 1:
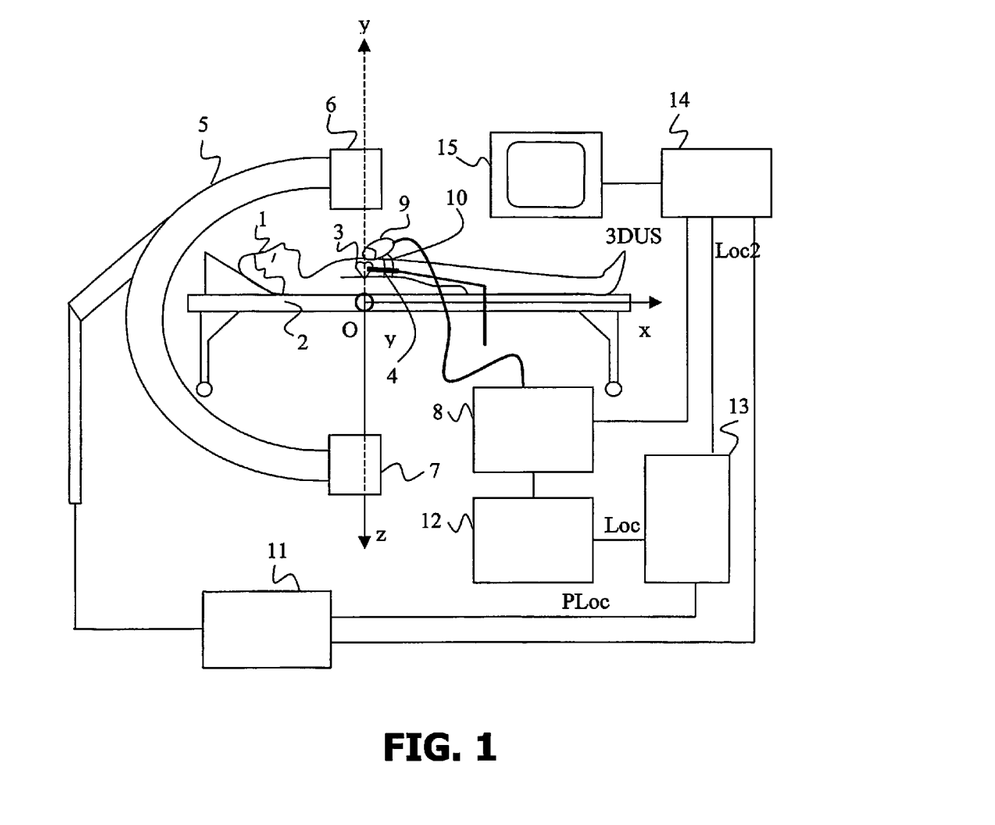
FIG. 1 is a schematical drawing of a system in accordance with the invention.

The schematical drawing of FIG. 1 shows a patient 1, who is arranged on a patient table 2 and whose symbolically indicated heart 3 is subjected to a treatment by means of a catheter 4 introduced into the body. The system comprises means 5 for acquiring a 2D X-ray image of the patient body. Said X-ray acquisition means comprise a focal X-ray source 6 and a detector 7. Advantageously, these X-ray acquisition means 5 are a C-arm system, as it is usually the case in a cathlab room. An advantage of such a C-arm system is to be able to have a rotational motion around the patient body in order to produce a plurality of 2D X-ray images of the patient at known orientation angles.

The system in accordance with the invention further comprises means 8 for acquiring a 3D ultrasound data set from an ultrasound probe 9, which has been placed on the patient body and fixed by fixation means, for instance a belt 10 or a stereotactic arm. It should be noted that both 2D X-ray image and 3D ultrasound data set are acquired in real-time, which enables a live visualization of the medical instrument, when it is guided inside the patient body.

The X-ray acquisition means 5 are associated with a referential of coordinates (O, x, y, z), called X-Ray referential hereinafter, in which the geometry of the focal X-ray source 6 and the detector 7 is known. It should be noted that the X-Ray referential (O, x, y, z) is bound to the fixed part of the X-Ray acquisition means and not to the C-arm. Therefore, the orientation of the C-arm can be expressed in said X-Ray referential. However, the geometry of the X-Ray acquisition means is dependent on a particular position of the C-arm.

The system in accordance with the invention further comprises means 11 for localizing the ultrasound probe 9 within the X-Ray referential (O, x, y, z), means 12 for selecting a region of interest around the medical instrument in the 3D ultrasound data set and for providing a first localization $Loc_1$ of the region of interest within a referential (O', x', y', z') of the ultrasound acquisition means, means 13 for converting the first localization $Loc_1$ of the region of interest within a referential (O', x', y', z') into a second localization $Loc_2$ of the region of interest within the X-Ray referential (O, x, y, z) and means for generating a bimodal representation BI by combining data from the 2D X-ray image with the 3D ultrasound data included in the region of interest and localized by the second localization $Loc_2$. The bimodal representation BI is displayed on a screen 15.

Figure 2:
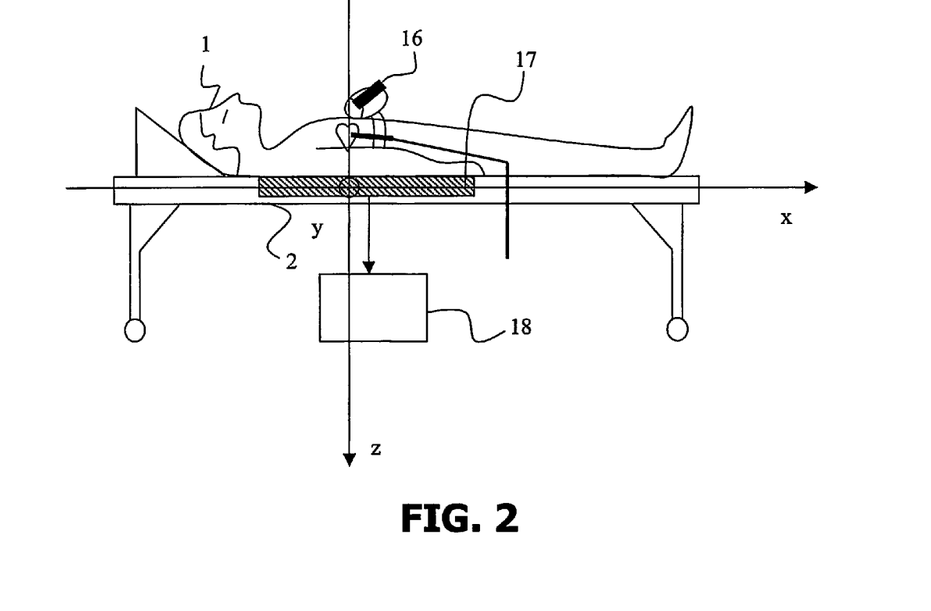
FIG. 2 is a schematical drawing of means for localizing the ultrasound probe within the X-ray referential, when the ultrasound probe is equipped with active localizers.

Referring to FIG. 2, the probe localization means 11 are, in a first approach, based on an active localizer 16, well-known to those skilled in the art, which is arranged on the ultrasound probe 9. Said active localizer 16, for instance an RF coil, is intended to transmit an RF signal to an RF receiving unit 17 placed under the patient body and for instance integrated into the table. The RF receiving unit transmits the received signal to measuring means 18 for measuring a position of the ultrasound probe 9 in a known referential, for instance the referential (O, x, y, z) of the X-ray acquisition means 5. It should be noted that the active localizer 16 must be two-dimensional and placed on the ultrasound probe 9 in such a way that a precise measurement of the position and of the orientation of the ultrasound probe can be calculated. It should be noted that a led-based optical localizer could be used as well. A first advantage of this first approach is that it provides a precise localization of the ultrasound probe. A second advantage is that it is performed in real-time and therefore, can be triggered during the clinical procedure.

Figure 3:
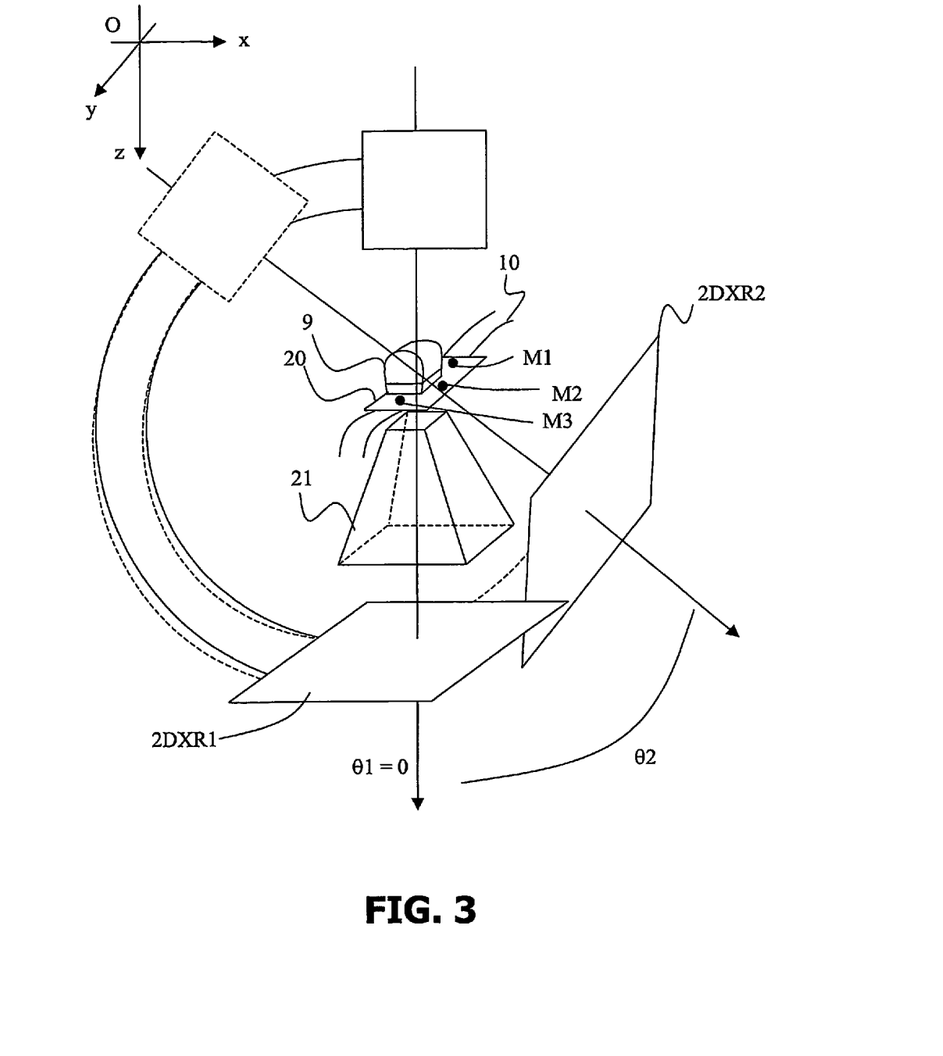
FIGS. 3, 4a and 4b are schematical drawings of means for localizing the ultrasound probe within the X-ray referential, when the probe is equipped with a belt comprising radio-opaque markers.

In a second approach of the probe localization means 11 shown in FIG. 3, the ultrasound probe 9 is fixed around the body of the patient 1 with a belt 10 equipped with at least three non aligned interdependent radio-opaque markers $M_1$, $M_2$ and $M_3$. For instance, the belt 10 comprises a plexiglas plaque, in which the three non aligned interdependent radio-opaque markers are fixed.

The three markers $M_1$, $M_2$ and $M_3$ belong to a same plane, therefore at least one 2D X-ray projection $2DXR_1$ acquired with an orientation angle $\theta_1$ of the C-arm system 5 is needed in order to determine the position of the ultrasound probe in the X-Ray referential (O, x, y, z). However, since the three markers are interdependent, and non-aligned, which means that they form a rigid tetraedre, it is well-known to those skilled in the art that the position of the probe is completely specified by the X-ray projection $2DXR_1$.

Figure 4A:
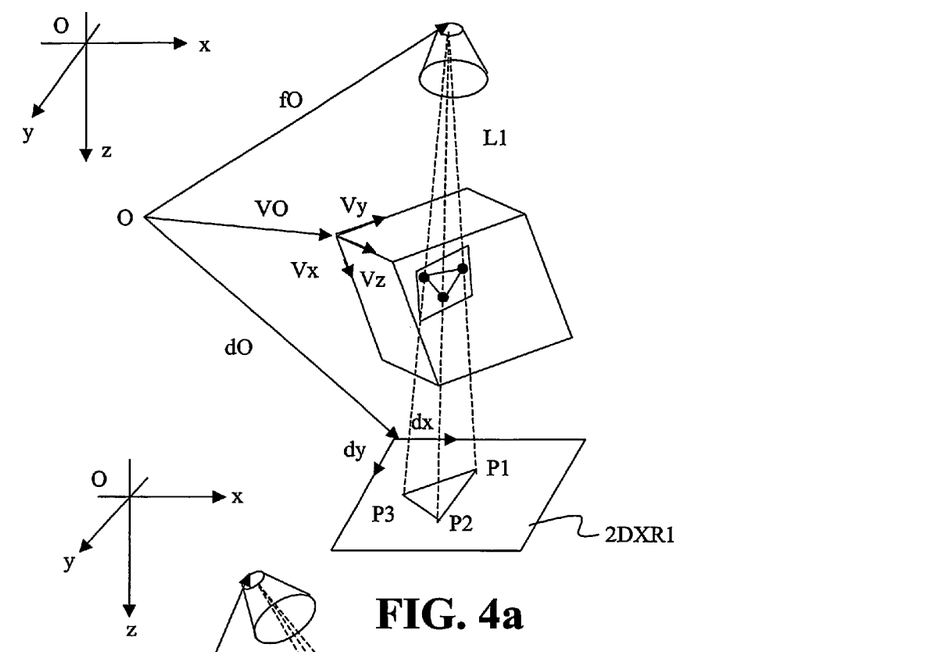

Referring to FIG. 4a, we consider a detector referential (dO, dx, dy). Six parameters like for instance the coordinates $(dx_1, dy_1)$, $(dx_2, dy_2)$, $(dx_3, dy_3)$ of the projections $P_1$, $P_2$, $P_3$ of the three markers $M_1$, $M_2$ and $M_3$ in the first 2D X-ray image $2DXR_1$ do completely specify the position of the ultrasound probe 9 in the X-Ray referential (O, x, y, z). A first advantage of using radio-opaque markers $M_1$, $M_2$ and $M_3$ is that they appear in a 2D X-Ray projection with a very high contrast, which facilitates their localization. Such a localization may be achieved manually or automatically. In the manual case, a user may click on at least two radio-opaque markers in each 2D X-ray image. In the automatical case, image processing techniques well known to those skilled in the art, like for instance a morphological filter, may be used for detecting the radio-opaque markers, which appear as highly contrasted blobs in the 2D X-ray projections. A second advantage is that such a localization is performed in real-time and therefore does not imply any peri-interventional step. It should be noted however that there is a priori no need to displace the ultrasound probe during the clinical procedure, because medical data are intended to be used once the medical instrument has been guided in a cavity of the patient body to be investigated. A third advantage is that it does not introduce metallic objects in the field of view of the X-Ray and ultrasound acquisition means.

Figure 4B:
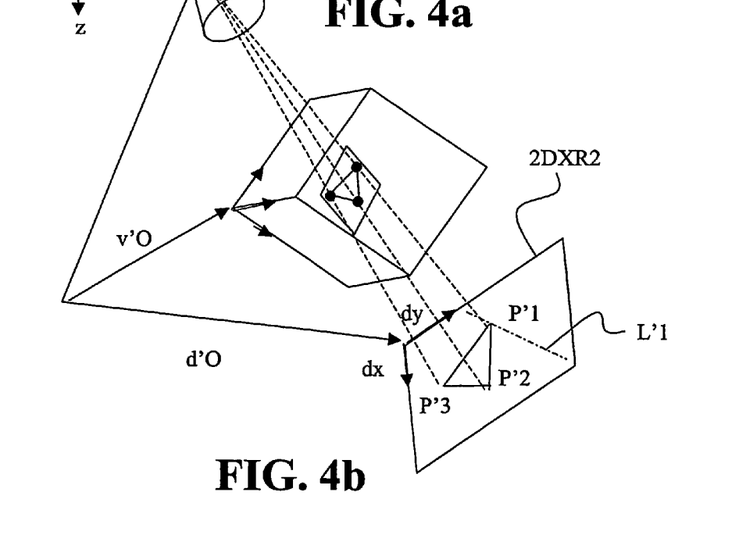

In an alternative to the second approach, a second 2D X-Ray image 2DXR$_2$ is acquired with a second orientation angle θ$_2$ of the C-arm system 5, as shown in FIG. 4B. This second X-Ray image allows to determine the coordinates (dx'$_1$, dy'$_1$), (dx'$_2$, dy'$_2$), (dx'$_3$, dy'$_3$) of a new set of projections P'$_1$, P'$_2$, P'$_3$ of the three markers M$_1$, M$_2$ and M$_3$. It should be noted that the localized points P$_1$, P$_2$, P$_3$ and P'$_1$, P'$_2$ and P'$_3$ follow epipolar constraints: this means for instance that a line L$_1$ linking the source focal point to the point P$_1$ appears as a projected line L'$_1$ in the second X-ray image 2DXR$_2$, which comprises P'$_1$. A first advantage is that P'$_1$ has not to be searched within the whole image, but only on the projected line L'$_1$. A second advantage is that it gives a way of associating the points P$_1$, P$_2$, P$_3$ and P'$_1$, P'$_2$, P'$_3$ with the right markers M$_1$, M$_2$ and M$_3$.

Such a localization of the ultrasound probe 9, which involves two 2D X-Ray images is not performed in real-time and has therefore to be handled in a peri-interventional step of the clinical procedure. An advantage of acquiring two 2D X-Ray images is that the precision of the localization is greatly increased.

Once the ultrasound probe 9 has been located in the X-Ray referential (O, x, y, z), an orientation of the probe is known and therefore, the location of the 3D ultrasound data set 22, also called 3D ultrasound cone, can be deduced. This is achieved by the converting means 13 which calculate a position of a point of said 3D ultrasound data set in the X-Ray referential from said ultrasound probe localization. A projection of said point on the detector in accordance with the geometry of the X-Ray acquisition means can also be deduced.

Figure 5:
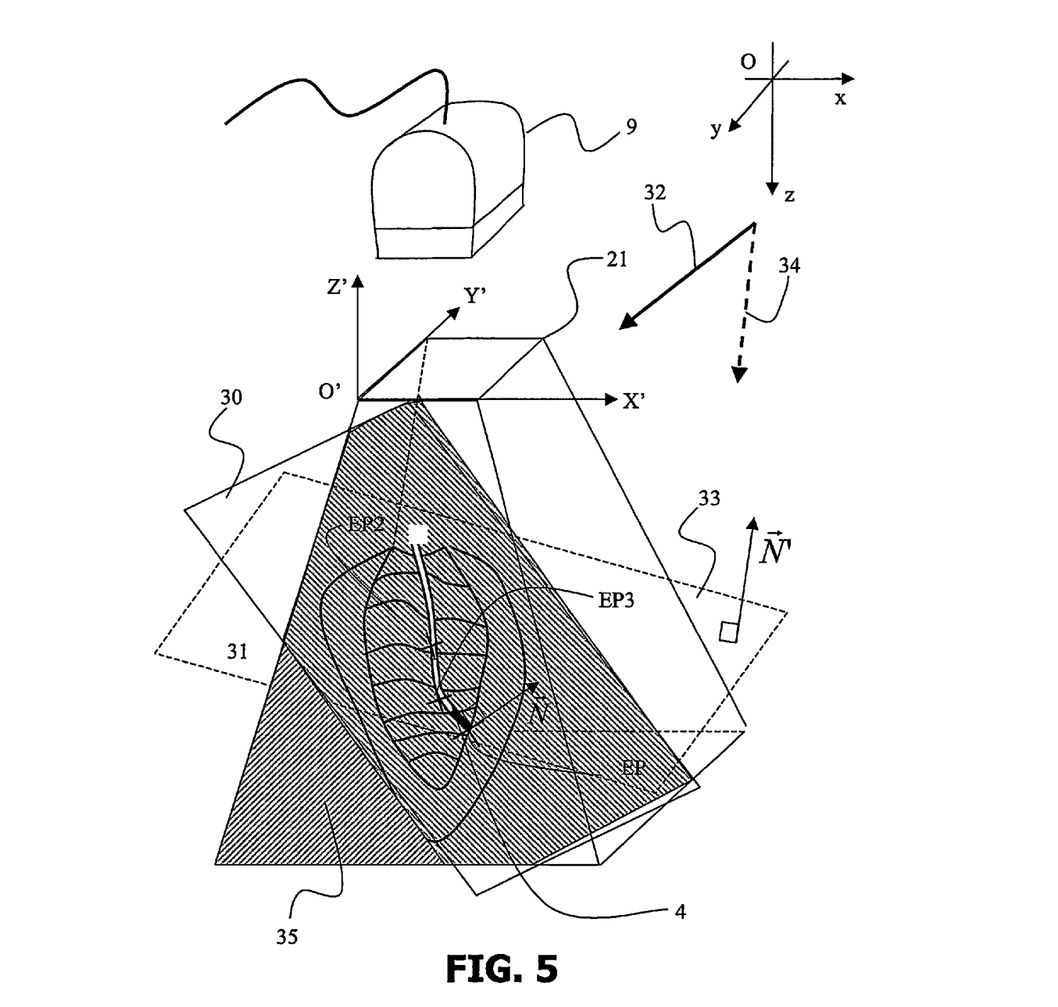
FIG. 5 is a schematical drawing of means for localizing the medical instrument and determining a plane comprising said medical instrument within the 3D ultrasound data set in accordance with the invention.

Referring to FIG. 5, the system in accordance with the invention comprises means 12 for selecting a region of interest 35 around the medical instrument 4 within the 3D ultrasound data set 21. A reference plane comprising a part of the medical instrument is defined. Advantageously, said reference plane is chosen perpendicular to the direction of orientation of the X-Ray acquisition means. The region of interest is obtained by cropping a 3D ultrasound data subset, which lies behind said reference plane or by cropping a slab which is formed around said reference plane. In this way, structures which could occlude the visibility of medical instrument in the 3D ultrasound data set are removed. In a first approach, the user interactively selects the region of interest 35 in the 3D ultrasound data set. In a second approach, a location of said reference plane can be predefined, for instance at a predefined reference depth equal to a third of the depth of the 3D data set. This predefined reference plane may be further rotated for searching a viewing angle view within the 3D ultrasound data set from which the medical instrument is more visible. A rotated reference plane 33 is obtained. Advantageously said viewing angle is applied to the C-arm system in order to optimize the 2D X-ray image.

Advantageously the selection means 12 comprise means for detecting the medical instrument 4 within the 3D ultrasound data set 21. It should be noted that a medical instrument usually appears with a high contrast within the 3D ultrasound data set. It is for instance the case of an electrophysiology catheter, which comprises a metal tip at its extremity. Said tip is a small and thin segment, which is very echogen and leaves a specific signature in the 3D ultrasound data set. Therefore, either the tip end is considered as a punctual landmark or the whole tip is considered as an elongated landmark.

Consequently, said detection means involve image processing techniques, which are well known to those skilled in the art, for enhancing either a highly contrasted blob or elongated shape in a relatively uniform background.

The detection means allow to automatically define the reference plane 30 by a point EP$_1$ and a normal orientation $\vec{N}$, where the point EP$_1$ for instance corresponds to the detected extremity of the medical instrument, for instance the end of the tip 31, and the normal orientation $\vec{N}$ to the known orientation 32 of the X-ray source 6.

In an alternative the reference plane 33 is defined by at least three non aligned points EP$_1$, EP$_2$ and EP$_3$ given by the detection of the medical instrument 4. A second normal $\vec{N}'$ is defined, which can advantageously serve for reorienting the X-ray source 6 in order to optimize the X-ray acquisition with respect to the detected position of the medical instrument 4.

Figure 6:
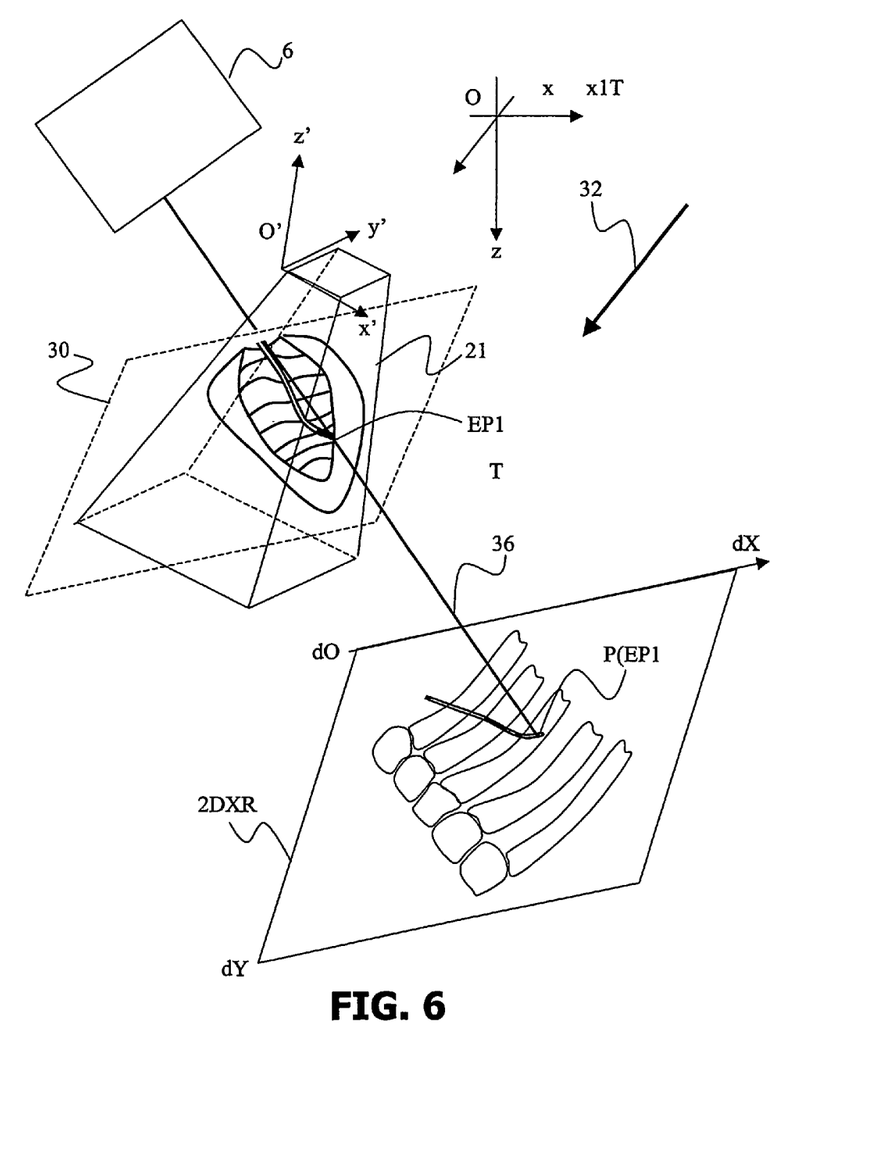
FIG. 6 is a schematical drawing of the converting means for converting a first localization of the region of interest within the referential of the ultrasound acquisition means into a second localization of the region of interest within the referential of the X-Ray acquisition means.

Referring to FIG. 6, a mapping between points included into the reference plane 30, 33 and points included into the 2D X-ray image 40 can be calculated from the knowledge of the geometry of the X-Ray acquisition means and of the second localization of the ultrasound probe 9 within the X-Ray referential (O, x, y, z) provided by the converting means 13. For instance, the point EP$_1$ is projected on a point P(EP$_1$) in the 2D X-Ray image 40 in accordance with a projection line 36.

The generation and display means 14 in accordance with the invention are intended to generate a bimodal representation of the medical instrument, in which information coming from both the 2D X-ray image and the 3D ultrasound data set are combined.

Figure 7:
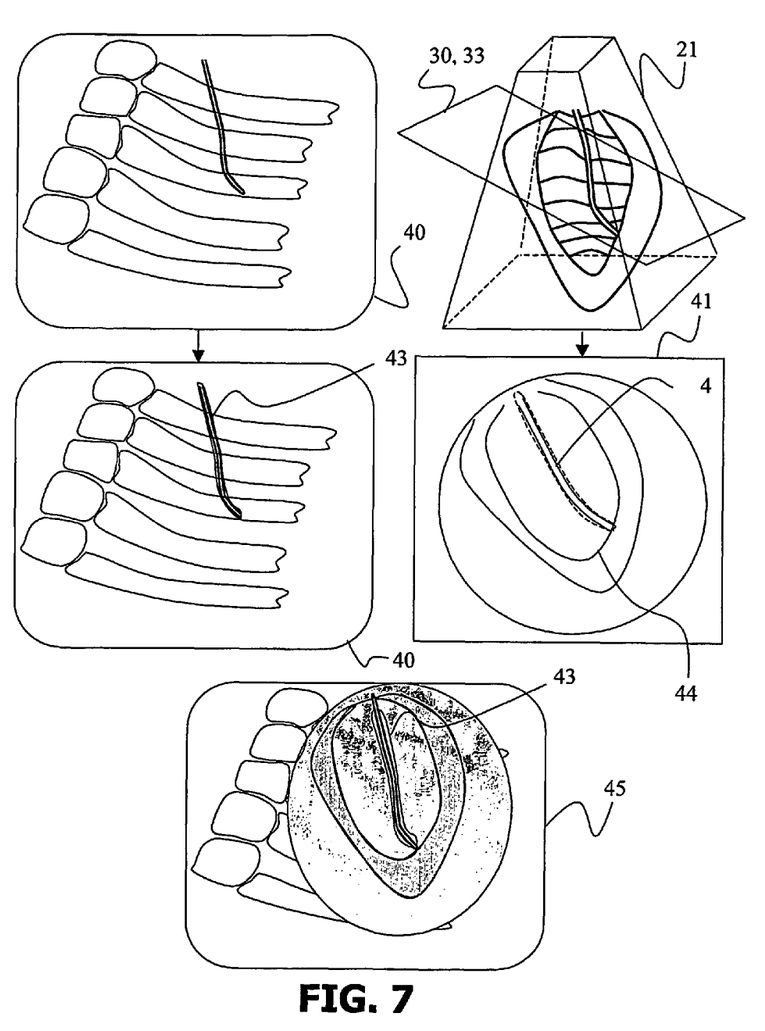
FIG. 7 is a schematical drawing of means for generating a bimodal representation in accordance with a first embodiment of the invention.

Preferably, such a combination is X-ray driven, which means that it is made on the basis of a 2D X-ray image 40, as shown in FIG. 7.

In a first embodiment of the invention, the region of interest of the medical instrument is included into the reference plane 30, 33. Therefore, the ultrasound information contained in the region of interest corresponds to a 2D ultrasound view 41, which is obtained by sampling the 3D ultrasound data set over the reference plane 30, 33.

The bimodal representation is an image formed such that the intensity values of all the points of the 2D X-ray projection 40 which have a corresponding point in the 2D ultrasound view 41 are combined. Such a combination is for instance defined by a scalar function f of a first intensity value I$_1$ of a point of the 2D X-Ray image 40 and a second intensity value I$_2$ of the corresponding point in the 2D ultrasound view 41. Such a scalar function f provides an intensity value I, for instance, by implementing an alpha-blending technique, which is well-known to those skilled in the art, in the following way:

$$I=f(I_1,I_2)=\alpha I_1+(1-\alpha)I_2$$

If α is equal to one, then the intensity value I of the bimodal representation is equal to the first X-Ray intensity I$_1$. On the contrary, if α is equal to zero, the intensity value I of the bimodal representation is equal to the second ultrasound intensity I$_2$, which means that the intensity value of the point of the 2D X-ray image is replaced by the intensity value of the corresponding point of the 2D ultrasound image 41.

The ultrasound acquisition means provide a 3D ultrasound data set which is focused on the medical instrument. With the invention, the combination of the X-Ray and ultrasound intensity values has the advantage to improve the visibility of the tissues surrounding the medical instrument.

It is well known to those skilled in the art that the projection of the medical instrument given by the X-ray source 7 on the detector 7 is of good quality and benefits from high resolution and contrast. When a detection of the medical instrument within the region of interest of the 3D ultrasound data set has been made available by the detection means, then a position of the projection of the medical instrument 4 within the 2D X-ray projection 40, that is in the detector referential (dO, dx, dy), can be derived from the position of the medical instrument in the X-Ray referential (O, x, y, z). This position is for instance a set 43 of points of the X-ray projection corresponding to a set of points 42 within the 2D ultrasound view 41.

Advantageously, the intensity values of the points of the 2D X-ray projection 40 belonging to the detected medical instrument are given to the corresponding points of the bimodal representation. An advantage is to keep the good visibility and resolution of the medical instrument provided by the X-ray acquisition means.

Figure 8:
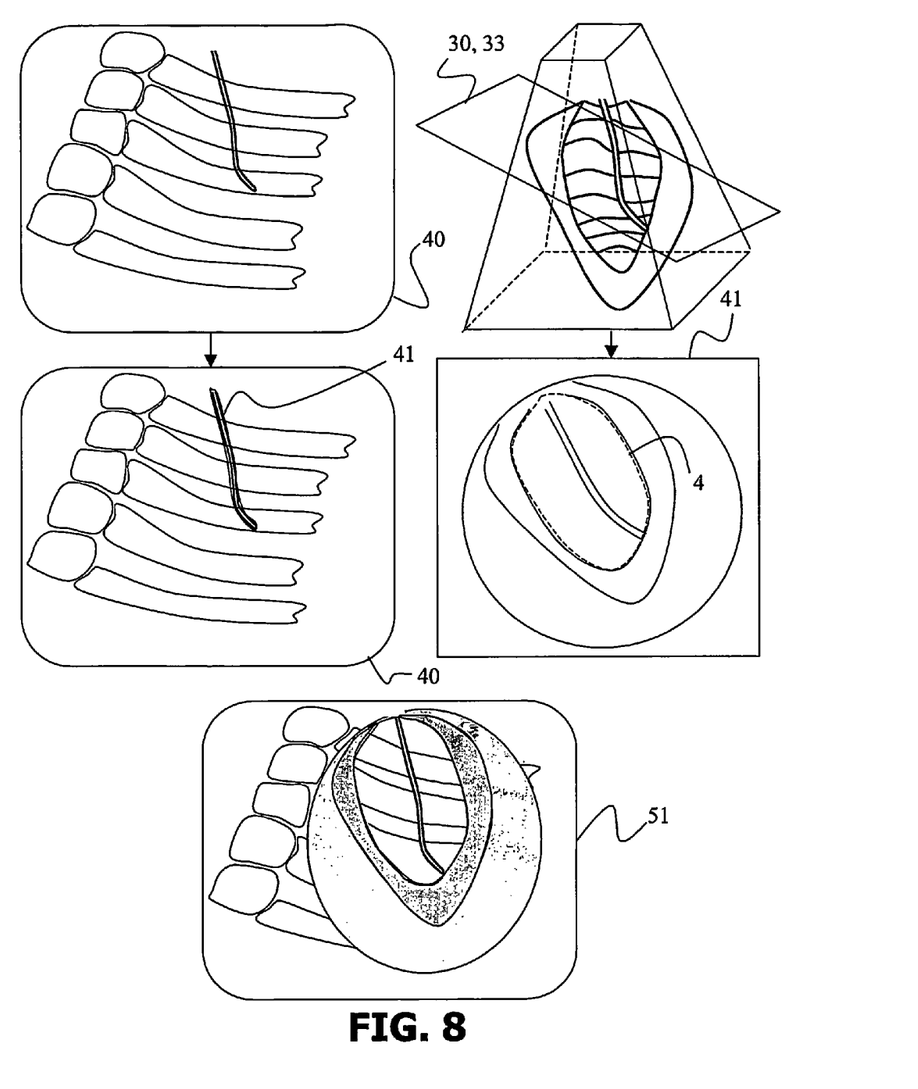
FIG. 8 is a schematical drawing of means for generating a bimodal representation in accordance with a second embodiment of the invention.

In a second embodiment of the invention shown in FIG. 8, the system in accordance with the invention further comprises means for segmenting a wall tissue region, for instance the endocardiac wall 44 in the neigbourhood of the medical instrument 4. This is achieved by image processing techniques such as intensity value thresholding, since wall tissues like myocardium appear brighter than blood in ultrasound images.

Another possibility is to detect borders, for instance by using an active contour technique (also called "snake"). This technique, well known to those skilled in the art, firstly consists in defining an initial contour and secondly in making said initial contour evolve under the influence of internal and external forces. A final contour 46 is obtained. It is then possible to differentiate points located inside from points located outside the contour 46 and to only give to the outside points the intensity values of the corresponding points of the 2D ultrasound view 41. An advantage of this second embodiment is to benefit from X-ray information in a larger surrounding of the medical instrument 4.

Figure 9:
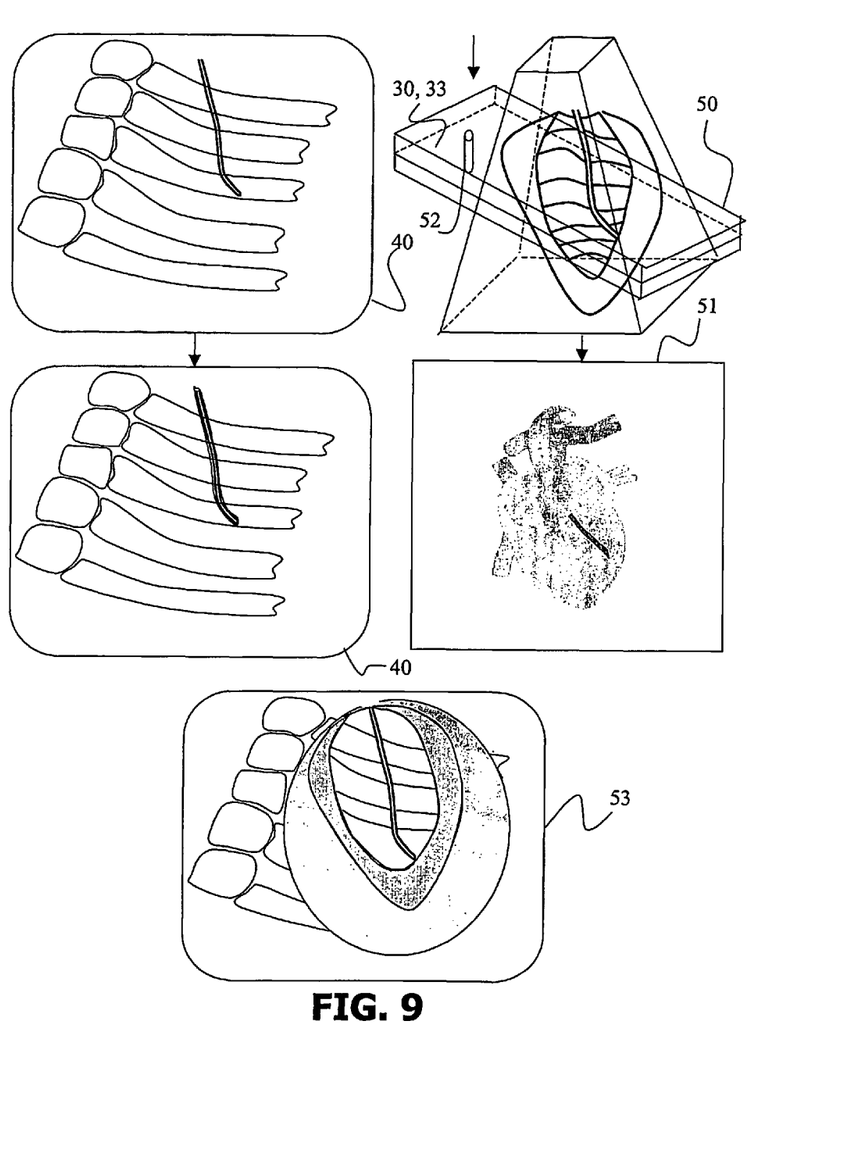
FIG. 9 is a schematical drawing of means for generating a bimodal representation in accordance with a third embodiment of the invention.

In a third embodiment of the invention schematically presented in FIG. 9, the system in accordance with the invention further comprises means for generating a volume rendered image 51 of the defined region of interest 35. In the present example, the region of interest 35 is a slab 50. The volume rendered image 51 is obtained by integrating the 3D ultrasound data in accordance with a direction, for instance the direction of orientation of the X-Ray acquisition means, as illustrated by the cylinder 52. Said volume rendered image 51 is used instead of the 2D ultrasound view 41 and combined with the 2D X-ray image 40 for generating a bimodal representation 53 in a similar way as previously described. An advantage of this third approach is to provide a perspective view of the neighbourhood of the medical instrument 4, which are for instance the heart cavities.

It should be noted that the generation means 14 could inversely generate a bimodal representation on the basis of the 3D ultrasound data set and replace X-ray information by ultrasound information. However, it is of less interest, because in this case, the bimodal representation has an image field which is reduced to the one of the 3D ultrasound acquisition means.

The system is intended to provide both a live 2D X-Ray image and a live 3D ultrasound data set. Although a localization of the probe has already been performed in a peri-interventional step, it could be necessary to update such a localization when patient movements occur, in particular if the respiratory movements have to be compensated for. As a matter of fact, a patient movement may cause a change of position of the ultrasound probe within the X-Ray referential and therefore induce errors when mapping the 2D X-Ray data with the 3D ultrasound data. Therefore, in a fourth embodiment of the invention, the system comprises controlling means for periodically triggering the means for localizing the ultrasound probe within the X-Ray referential. Such a triggering can be performed manually, when the user judges it necessary or automatically at regular time intervals, to the extent of retriggering this probe localization for every new 2D X-Ray image or 3D ultrasound data set acquired. It should be noted that in this case, the probe localization has to be performed in real-time. An advantage is that it avoids any accumulation of errors when mapping the 2D X-Ray data with the 3D ultrasound data.

Figure 10:
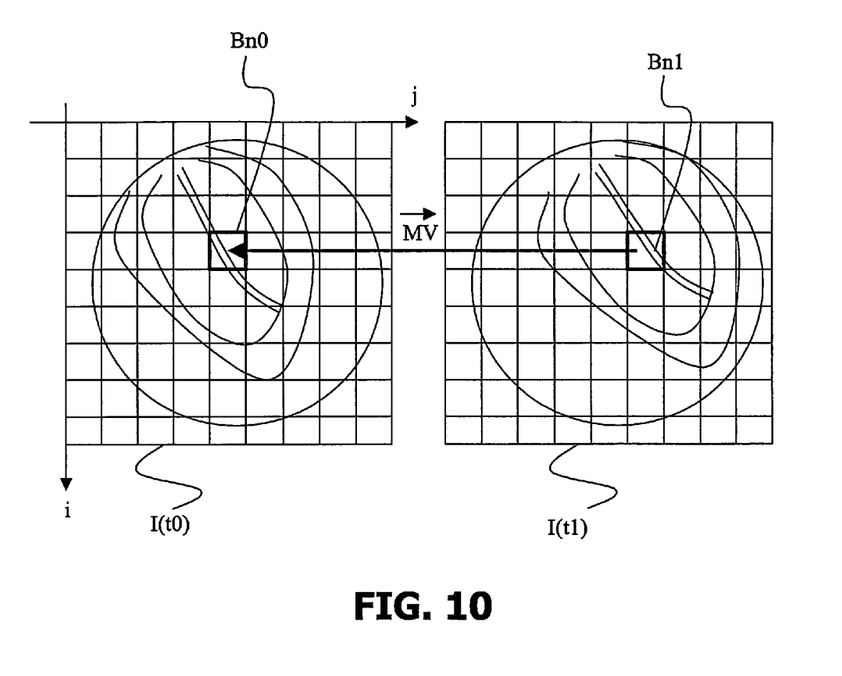
FIG. 10 is a schematical drawing of means for compensating a motion between a current 3D ultrasound data set acquired at a current time and a previous 3D ultrasound data set acquired at a previous time.

In a fifth embodiment of the invention, the system comprises means for compensating any relative motion of the ultrasound probe with respect to the patient heart in the interval between two successive probe localizations. These motion compensation means are intended to compensate a motion between a current 3D ultrasound data set $3DUS(t_0+t)$ acquired at a current time $t_0+t$ and a previous 3D ultrasound data set $3DUS(t_0)$ acquired at a previous time $t_0$, both ultrasound data sets corresponding to a same phase of the heart cycle. Firstly, motion vectors linking points of the current 3D ultrasound data set $3DUS(t_0+t)$ with points of the previous 3D ultrasound data set $3DUS(t_0)$ are estimated and the points of the current 3D ultrasound data set $3DUS(t_0+t)$ are displaced in accordance with the calculated motion vectors. Therefore, a motion compensated current 3D ultrasound data set $MC(3DUS(t_0+t))$ is obtained, which is expected to be closer to the previous 3D ultrasound data set $3DUS(t_0)$. In a first approach, a block-matching technique, well known to those skilled in the domain of video compression, is advantageously used. Referring to FIG. 10, which illustrates the principles of a block matching in the 2D case for simplicity reasons, the current and previous 3D ultrasound data sets $3DUS(t_0+t)$ and $3DUS(t0)$ are divided into blocks, for instance of 8×8×8 points and for each block $B_{n1}$ of the current 3D ultrasound data set a search of the block $B_{n0}$ of the previous 3D ultrasound data set is performed, which leads to a maximum of correlation. A motion vector $\overrightarrow{MV}=\overrightarrow{Bn_1Bn_0}$ is obtained.

Therefore the motion compensation means are intended to compensate in the current ultrasound image for small motions which may have occurred between time $t_0$ and time $t_0+t$. It should be noted that motion compensation is efficient when small differences exist between both 3D ultrasound data sets. An advantage of the fifth embodiment of the invention is to provide a solution for compensating errors of localization due to small movements of the probe with respect to the cavity to be explored, like the heart, which is compatible with live visualization. This solution is particularity advantageous when the probe localization cannot be performed in real-time, for instance when several angular views provided by the C-arm are involved. In this case, the motion compensation means may be advantageously used in the mean time of two successive probe localizations.

It should be noted that the system in accordance with the invention has a particular interest for electrophysiology procedures, which consist either in generating an electrical activation map of a heart cavity wall for diagnosing heart diseases or in burning a zone of the wall tissue, which has been identified as abnormal. As a matter of fact, by providing a live visualisation of a large viewing field of the area of operation, in which the medical instrument, the bone structures and the surrounding wall tissues are simultaneously visible, the system in accordance with the invention facilites a generation of the electrical activation map.

Figure 11:
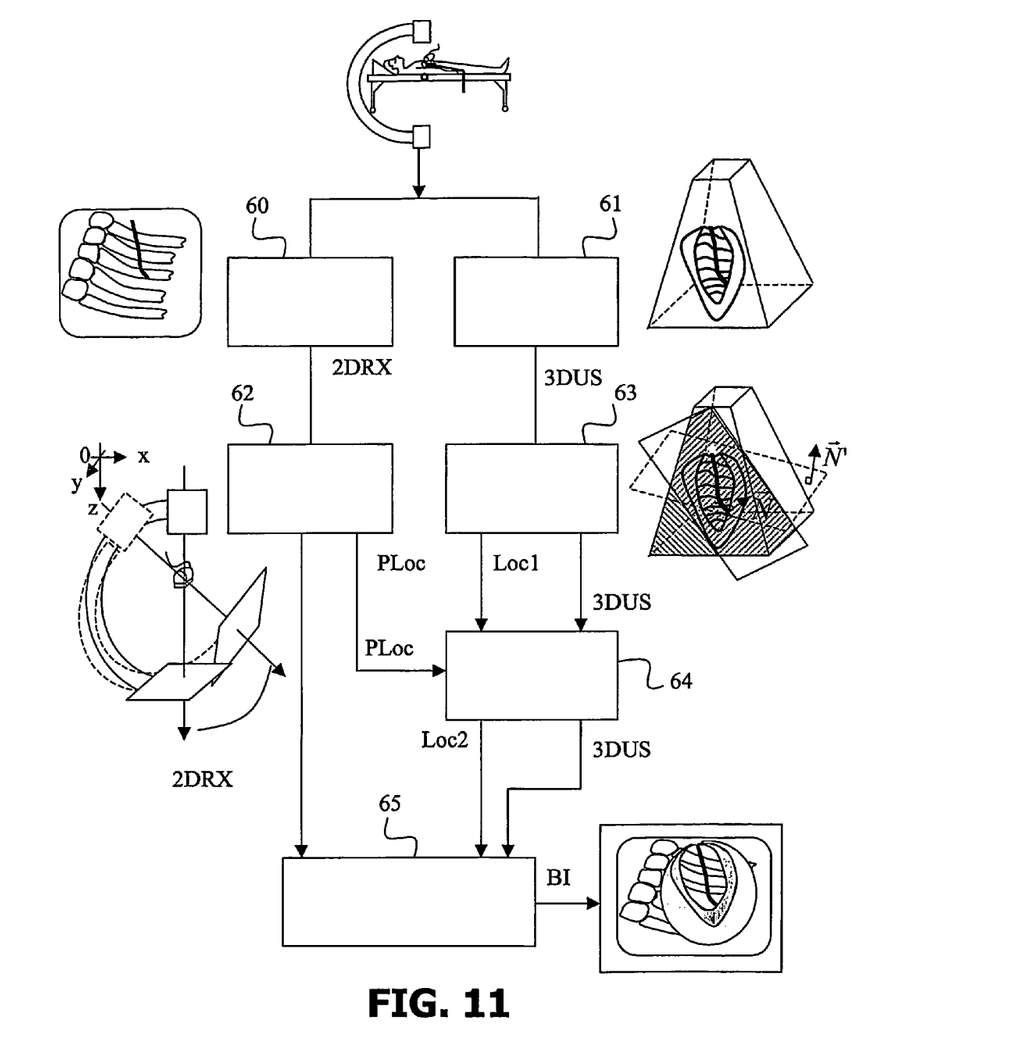
FIG. 11 is a functional diagram of the method in accordance with the invention.

The invention also relates to a method of guiding a medical instrument 4 in a patient body. Referring to FIG. 11, such a method comprises the steps of:
  acquiring 60 a two-dimensional X-ray image of said medical instrument using an X-ray acquisition system, acquiring 61a three-dimensional ultrasound data set of said medical instrument using said ultrasound probe, localizing 62 said ultrasound probe in a referential of said X-ray acquisition system, selecting 63 a region of interest of said medical instrument within said 3D ultrasound data set and providing a first localization of said region of interest within a referential of the ultrasound acquisition means, converting 64 said first localization within said referential of the 3D ultrasound data set into a second X-Ray localization within said referential of the X-ray acquisition system, generating 65 and displaying a bimodal representation of said medical instrument in which both 2D X-ray image and the 3D ultrasound data included in said region of interest are combined using said second localization.

The drawings and their description hereinbefore illustrate rather than limit the invention. It will be evident that there are numerous alternatives, which fall within the scope of the appended claims. In this respect the following closing remarks are made: there are numerous ways of implementing functions by means of items of hardware or software, or both. In this respect, the drawings are very diagrammatic, each representing only one possible embodiment of the invention. Thus, although a drawing shows different functions as different blocks, this by no means excludes that a single item of hardware or software carries out several functions, nor does it exclude that a single function is carried out by an assembly of items of hardware or software, or both.

Any reference sign in a claim should not be construed as limiting the claim. Use of the verb "to comprise" and its conjugations does not exclude the presence of elements or steps other than those stated in a claim. Use of the article "a" or "an" preceding an element or step does not exclude the presence of a plurality of such elements or steps.

The invention claimed is:

1. A medical system comprising:
a medical instrument to be guided in a patient body,
an X-Ray acquisition system which acquires a two-dimensional X-ray image of said medical instrument,
an ultrasound acquisition system for acquiring a three-dimensional ultrasound data set of said medical instrument using an ultrasound probe,
a localizer which provides a localization of said ultrasound probe within a referential of said X-ray acquisition system,
a selector operable to selecting a region of interest around said medical instrument in the three-dimensional ultrasound data set, that defines a first localization of said region of interest within a referential of said ultrasound acquisition system,
a convertor which converts said first localization of said region of interest within said referential of the ultrasound acquisition system into a second localization of said region of interest within said referential of the X-ray acquisition system, using said localization of the ultrasound probe,
a generation and display screen which displays a bi-modal representation of said medical instrument in which said two-dimensional X-ray image and the three-dimensional ultrasound data included in said region of interest are combined using said second localization.

2. A system as claimed in claim 1, wherein said selector is operable to select a region of interest intended to define a reference plane in which a part of said medical instrument is included.

3. A system as claimed in claim 2, wherein said region of interest is a 2D ultrasound image obtained by sampling said 3D ultrasound data set over said reference plane.

4. A system as claimed in claim 2, wherein said region of interest is obtained by cropping a 3D ultrasound data subset, which lies behind said reference plane or by cropping a slab which is formed around said reference plane.

5. A system as claimed in claim 4, wherein said generation and display screen is intended to generate a volume rendered view of said region of interest within said 3D ultrasound data set.

6. A system as claimed in claim 1, wherein said localizer is intended to localize an active localizer, which has been arranged on said ultrasound probe.

7. A system as claimed in claim 1, wherein said ultrasound probe is equipped with at least three non aligned and interdependent radio-opaque markers and
said localizer is intended to localize said markers in at least a first 2D X-ray image having a first orientation angle in said referential.

8. A system as claimed in claim 7, wherein said localizer is intended to further localize said markers in a second 2D X-ray image having a second orientation angle in said referential.

9. A system as claimed in claim 1, wherein said selector is operable to detect said medical instrument within said region of interest of the 3D ultrasound data set and
said generation and display screen is intended to give to the points of the detected medical instrument in said bimodal representation the X-ray intensity values of the corresponding points in the 2D X-Ray image.

10. A system as claimed in claim 1, comprising
a segmenter operable to segment a wall tissue region in the 3D ultrasound data set and
said generation and display screen is intended to give to the points belonging to said wall tissue region the ultrasound intensity values of the corresponding points of said region of interest.

11. A system as claimed in claim 1, wherein the X-Ray acquisition system is intended to provide live two-dimensional X-Ray images and the ultrasound acquisition system live three-dimensional ultrasound data sets.

12. A system as claimed in claim 11, comprising a controller for periodically triggering the probe localizer.

13. A system as claimed in claim 11, comprising
a compensator operable to compensate a motion between a current three-dimensional ultrasound data set acquired at a current time and a previous three-dimensional ultrasound data set acquired at a previous time.

14. A method of guiding a medical instrument in a patient body, comprising the steps of:
acquiring a two-dimensional X-ray image of said medical instrument using an X-ray acquisition system,
acquiring a three-dimensional ultrasound data set of said medical instrument using said ultrasound probe and an ultrasound acquisition system,
localizing said ultrasound probe in a referential of said X-ray acquisition system,
selecting a region of interest of said medical instrument within said 3D ultrasound data set, that define a first localization of said region of interest within a referential of said ultrasound acquisition system,
converting said first localization within said referential of said ultrasound acquisition system into a second X-Ray localization within said referential of the X-ray acquisition system,
generating and displaying a bimodal representation of said medical instrument in which said two-dimensional X-ray image and the three-dimensional ultrasound data included in said region of interest are combined using said second localization.

* * * * *